United States Patent [19]
Boothe et al.

[11] Patent Number: 5,716,478
[45] Date of Patent: Feb. 10, 1998

[54] APPARATUS AND METHOD FOR APPLYING DISCRETE PARTS ONTO A MOVING WEB

[75] Inventors: Judson Lamar Boothe; Peter James Krautkramer, both of Appleton; Gary Alan Krueger, Neenah, all of Wis.

[73] Assignee: Kimberly-Clark Worldwide, Inc., Neenah, Wis.

[21] Appl. No.: 544,370

[22] Filed: Oct. 17, 1995

[51] Int. Cl.$^6$ ............................................ B32B 31/00
[52] U.S. Cl. ........................... 156/302; 156/242; 156/265; 156/270
[58] Field of Search .......................... 156/519, 570, 156/164, 269, 265, 302, 495, 520, 270, 297, 299, 494, 475, 489, 552, 242, 324

[56] References Cited

U.S. PATENT DOCUMENTS

| | | | |
|---|---|---|---|
| 3,963,557 | 6/1976 | Patterson | 156/519 |
| 4,061,527 | 12/1977 | Traise | 156/519 |
| 4,297,157 | 10/1981 | Van Vliet | 156/164 |
| 4,464,217 | 8/1984 | Dickover et al. | 156/164 |
| 4,479,836 | 10/1984 | Dickover et al. | 156/164 |
| 4,486,192 | 12/1984 | Sigl | 604/385 |
| 4,488,923 | 12/1984 | Pieniak | 156/199 |
| 4,523,969 | 6/1985 | Spencer | 156/161 |
| 4,572,043 | 2/1986 | Bianco | 83/18 |
| 4,578,133 | 3/1986 | Oshefsky et al. | 156/164 |
| 4,608,115 | 8/1986 | Schroth et al. | 156/519 |
| 4,610,751 | 9/1986 | Eschler | 156/517 |
| 4,617,082 | 10/1986 | Oshefsky et al. | 156/447 |
| 4,642,150 | 2/1987 | Stemmler | 156/164 |
| 4,648,928 | 3/1987 | Ales | 156/164 |
| 4,704,116 | 11/1987 | Enloe | 604/385 |
| 4,710,187 | 12/1987 | Boland et al. | 604/385 |
| 4,726,873 | 2/1988 | Ales et al. | 156/495 |
| 4,726,876 | 2/1988 | Tomsovic, Jr. | 156/552 |
| 4,762,521 | 8/1988 | Roessler et al. | 604/38 SA |
| 4,770,656 | 9/1988 | Proxmire et al. | 604/393 |
| 4,786,346 | 11/1988 | Ales et al. | 156/160 |
| 4,798,603 | 1/1989 | Meyer et al. | 604/378 |
| 4,925,520 | 5/1990 | Beaudoin et al. | 156/494 |
| 4,941,939 | 7/1990 | Nomura et al. | 156/495 |
| 5,091,039 | 2/1992 | Ujimoto et al. | 156/519 |
| 5,244,530 | 9/1993 | Collins et al. | 156/519 |
| 5,275,676 | 1/1994 | Rooyakkers et al. | 156/164 |

FOREIGN PATENT DOCUMENTS

| | | | |
|---|---|---|---|
| 2203358 | 5/1974 | France | B65C 9/00 |
| 3635387 A1 | 4/1987 | Germany | B65G 47/30 |
| WO 95/19752 A2 | 7/1995 | WIPO | A61F 13/15 |

OTHER PUBLICATIONS

Patent Cooperation Treaty Search Report from the International Search Authority, International Application No. PCT/US96/14382 dated Jan. 24, 1997.

*Primary Examiner*—Merrick Dixon
*Attorney, Agent, or Firm*—Jeffrey B. Curtin

[57] ABSTRACT

An apparatus and method for severing an elastic web traveling at a first speed into discrete parts and applying the parts onto a product web of interconnected disposable absorbent articles traveling at a second speed are disclosed. The apparatus includes a plurality of transfer segments which are configured to rotate about a common first axis. The apparatus also includes a drive ring which is configured to rotate about a second axis which is offset from the first axis of the transfer segments. A plurality of coupler arms are pivotally connected to the drive ring. As the drive ring is rotated, a cam end of each of the coupler arms is guided along a curvilinear path and a crank end of each of the coupler arms slidably engages a respective transfer segment thereby pivoting the coupler arms about the pivot points and rotating the transfer segments at a variable speed. The offset crank motion of the drive ring and the pivoting of the coupler arms independently varies an effective drive radius of each transfer segment to provide the desired variable speed.

23 Claims, 4 Drawing Sheets

FIG. 4

APPARATUS AND METHOD FOR APPLYING DISCRETE PARTS ONTO A MOVING WEB

BACKGROUND OF THE INVENTION

1. Field of the Invention

The present invention relates to an apparatus and method for receiving discrete parts traveling at a speed and applying the parts to a web traveling at a different speed. The invention more particularly concerns an apparatus and method for receiving discrete elongated elastic parts of a continuously moving web of elongated elastic material traveling at a certain speed and applying the discrete elongated elastic parts onto a product web of interconnected disposable absorbent articles traveling at a different speed.

2. Description of the Related Art

Articles, such as disposable diapers, generally have been manufactured by a process where discrete parts or components of different materials, such as leg elastic, waist elastic, tapes, and other fasteners such as hook and loop materials or snaps, have been applied to a continuously moving product web of interconnected articles. Often, the speed at which the parts are fed into the process is not the same as the speed of the product web itself. Thus, the speed of the parts must be changed to match the speed of the product web to properly apply the parts without adversely affecting the process or the finished articles.

Several different conventional methods for changing the speed of a part or component of material such that it can be applied to a continuously moving web have been known to those skilled in the art. For example, one method has been known as the slip gap or slip cut method. A web of material, which is traveling at a slower speed than the moving web, is fed into a knife and anvil roll having a surface speed equal to the speed of the moving web. As the material is cut into discrete parts, vacuum in the anvil roll is activated to draw the parts of material to the surface of the anvil roll. The anvil roll then carries the parts to the moving web where the vacuum is released and the parts are applied to the moving web while both the parts and the moving web are traveling at the same speed.

Another method has utilized festoons to reduce the speed of the moving web to match the speed of the discrete parts of material to be applied to the web. The moving web is temporarily slowed down to the speed of the parts with the excess portion of the moving web gathering in festoons. The parts of material are then applied to the moving web while both the parts and the web are traveling at the same speed. The festoons are then released allowing the moving web to return to its original speed.

Another method has utilized a slider-crank mechanism to accomplish the speed change. The slider-crank mechanism utilizes concentrically mounted arms or linkages to receive the discrete parts of material, increase the speed of the parts to match the speed of the moving web and apply the parts to the moving web. The slider-crank mechanism is a special case of a four bar linkage system.

Finally, another such method to change the speed of a discrete part before it is applied to a moving web has utilized a cam actuated crank-follower mechanism. The cam actuated crank-follower mechanism comprises crank levers that are mounted on a rotatable driving plate. Each crank lever includes a cam follower on one end and a follower lever connected to the other end. The other end of the follower lever is connected to an applicator device which is mounted concentric with the driving plate's center of rotation. The cam follower remains in contact with a fixed cam that is also mounted concentric with the driving plate's center of rotation. As the driving plate rotates, the crank levers pivot as their cam followers follow the cam shape. As the crank levers pivot, the follower levers cause the applicator devices to speed up or slow down. An example of this method is described in U.S. Pat. No. 4,610,751 issued Sep. 9, 1986, to Eschler.

Conventional methods, such as those described above, have exhibited several drawbacks. First, as the discrete parts of material are transferred, they are often subjected to a tugging action because the surface speed of the transfer means used to transfer the parts is greater than the speed of the parts. The tugging action may result in an undesirable elongation or tear of the parts. Second, several of the conventional methods provide substantial speed variations but do not provide any periods where the speed remains constant for a fixed duration. Thus, the discrete parts may be adversely affected because the surface speed of the transfer means used to transfer the parts is continuously changing during the receiving and application process. Finally, several of the conventional methods can be very expensive and time consuming to change as the size and speed of the discrete parts and the speed of the moving web change to coincide with various finished product sizes. Consequently, an inexpensive and adaptable apparatus for receiving discrete parts traveling at a speed and applying the parts to a web traveling at a different speed is desirable.

Moreover, it is desirable that the receiving and applying of the parts occurs while the respective surface speeds are maintained substantially constant for a fixed duration. For example, it is desirable to apply the parts to the substrate web while the parts and substrate web are traveling at substantially the same surface speed. Such a constant speed dwell allows precise control of the length and placement of the part on the substrate web especially if the part is fragile and/or elastic.

SUMMARY OF THE INVENTION

In response to the discussed difficulties and problems encountered in the prior art a new apparatus and method for receiving discrete parts traveling at a speed, changing the speed of the parts to match the speed of a continuously moving substrate web traveling at a different speed and applying the parts to the moving substrate web have been discovered.

In one aspect, the present invention concerns an apparatus for severing a first substrate web traveling at a first speed into discrete parts and applying the discrete parts onto a second substrate web traveling at a second speed. The apparatus includes at least one transfer segment which is configured to rotate about a first axis. The transfer segment includes an outer surface which is configured to receive the discrete parts and apply the discrete parts to the second substrate web. The apparatus also includes a drive ring which is configured to rotate about a second axis which is offset from the first axis of the transfer segment. At least one coupler arm is pivotally connected to the drive ring about a pivot point located radially outward from the second axis. The coupler arm includes a cam end which is configured to follow a predetermined curvilinear path and a crank end which is slidably connected to the transfer segment. A drive mechanism is configured to rotate the drive ring about the second axis. As the drive ring is rotated, the cam end of the coupler arm is guided along the curvilinear path and the crank end of the coupler arm slidably engages the transfer segment thereby pivoting the coupler arm about the pivot point to vary an effective drive radius of the transfer segment and rotate the transfer segment at a variable speed. In use, the transfer segment is configured to maintain a substantially constant first surface speed as the discrete parts are received and a substantially constant second surface speed as the discrete parts are applied to the second substrate web.

In another aspect, the present invention concerns an apparatus for severing an elongated elastic web traveling at a first speed into discrete elongated elastic parts and applying the elongated elastic parts onto a product web of interconnected disposable absorbent articles traveling at a second speed. The apparatus includes a plurality of transfer segments which are configured to rotate about a common first axis. The transfer segments include an outer surface which is configured to receive the elongated elastic parts and apply the elongated elastic parts to the product web. The apparatus also includes a drive ring which is configured to rotate about a second axis which is offset from the first axis of the transfer segments. A plurality of coupler arms are pivotally connected to the drive ring about a respective pivot point which is located radially outward from the second axis. Each of the coupler arms includes a cam end which is configured to follow a predetermined curvilinear path and a crank end which is slidably connected to a respective one of the transfer segments. A drive mechanism is configured to rotate the drive ring about the second axis. As the drive ring is rotated, the cam end of each of the coupler arms is guided along the curvilinear path and the crank end of each of the coupler arms slidably engages the respective transfer segment thereby pivoting the coupler arms about the pivot points and rotating the transfer segments at a variable speed. The offset crank motion of the drive ring and the pivoting of the coupler arms independently varies an effective drive radius of the transfer segments to provide the variable speed. In a particular aspect, the outer surface of the transfer segments may define a surface roughness of at least about 3 micrometers to maintain the elongated elastic parts in an elongated state.

In yet another aspect, the present invention concerns a method for serving a first substrate web traveling at a first speed into discrete parts and applying the discrete parts onto a second substrate web traveling at a second speed. The method includes the steps of: (a) supplying the first substrate web at the first speed and the second substrate web at the second speed; (b) severing the first substrate web into the discrete parts; (c) rotating at least one transfer segment about a first axis at a variable speed wherein the step of rotating includes the steps of: (i) providing a drive ring which is rotatable about a second axis which is offset from the first axis of the transfer segment; (ii) providing a coupler arm which is pivotally connected to the drive ring about a pivot point located radially outward from the second axis wherein the coupler arm includes a cam end which is configured to follow a predetermined curvilinear path and a crank end which is slidably connected to the transfer segment; and (iii) rotating the drive ring about the second axis thereby guiding the cam end along the curvilinear path and slidably engaging the crank end with the transfer segment to pivot the coupler arm about the pivot point to selectively vary an effective drive radius of the transfer segment and rotate the transfer segment at the variable speed; (d) transferring the discrete parts onto an outer surface of the transfer segment while the transfer segment is rotating at a first surface speed; and (e) applying the discrete parts onto the second substrate web while the transfer segment is rotating at a second surface speed.

In a particular aspect, the pivoting of the coupler arm maintains the first surface speed of the transfer segment substantially equal to the speed of the first substrate web as the discrete parts are received and maintains the second surface speed of the transfer segment substantially equal to the second speed of the second substrate web as the discrete parts are applied to the second substrate web. In such a configuration, the first surface speed and the second surface speed may be maintained substantially constant for at least 10 degrees of rotation of the transfer segment. The first surface speed and the second surface speed may further define a speed ratio of from about 0.1:1 to about 0.99:1.

In still another aspect, the present invention concerns a method for serving an elongated elastic web traveling at a first speed into discrete elongated elastic parts and applying the elongated elastic parts in a spaced apart relationship onto a product web of interconnected disposable absorbent articles traveling at a second speed. The method comprises the steps of: (a) supplying the elongated elastic web at the first speed and the product web at the second speed; (b) severing the elongated elastic web into the discrete elongated elastic parts; (c) rotating a plurality of transfer segments about a common first axis at a variable speed wherein said step of rotating includes the steps of: (i) providing a drive ring which is rotatable about a second axis which is offset from the first axis; (ii) providing a plurality of coupler arms each of which is pivotally connected to the drive ring about a respective pivot point which is located radially outward from the second axis wherein each of the coupler arms includes a cam end which is configured to follow a predetermined curvilinear path and a crank end which is slidably connected to a respective one of the transfer segments; and (iii) rotating the drive ring about the second axis thereby guiding said cam end along said curvilinear path and slidably engaging said crank end with said respective transfer segment to pivot each of the coupler arms about the respective pivot points to independently vary an effective drive radius of each of the transfer segments and rotate the transfer segments at the variable speed; (d) transferring each of the discrete elongated elastic parts onto an outer surface of the respective transfer segment while the respective transfer segment is rotating at a first surface speed which is substantially equal to the first speed of the elongated elastic web; and (e) applying each of the elongated elastic parts onto the product web while the respective transfer segment is rotating at a second surface speed which is substantially equal to the second speed of the product web. In a particular aspect, the method includes the step of maintaining the discrete elongated elastic parts at an elongation of at least 150 percent until they are applied to the product web.

As compared to conventional apparatus and methods, such as the slip gap method described above, for changing the speed of a discrete part such that it can be applied to a continuously moving web, the use of the combination of an eccentrically mounted drive means and a pivotal coupler arm provides the ability to obtain greater changes in speed and to maintain constant speeds for a fixed duration. Thus, the use of the present invention can provide a more precise control of the length and placement of the discrete part onto the moving web.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present invention provides an apparatus and method for receiving discrete parts traveling at a first speed and applying the parts to a substrate web traveling at a second speed. The apparatus and method are particularly useful for receiving discrete parts of an elastic material, such as leg or waist elastics, and applying the parts to a product web of interconnected disposable absorbent articles such as, for example, disposable diapers. It is readily apparent, however, that the apparatus and method would be suitable for applying any part to a substrate web.

Figure 1:
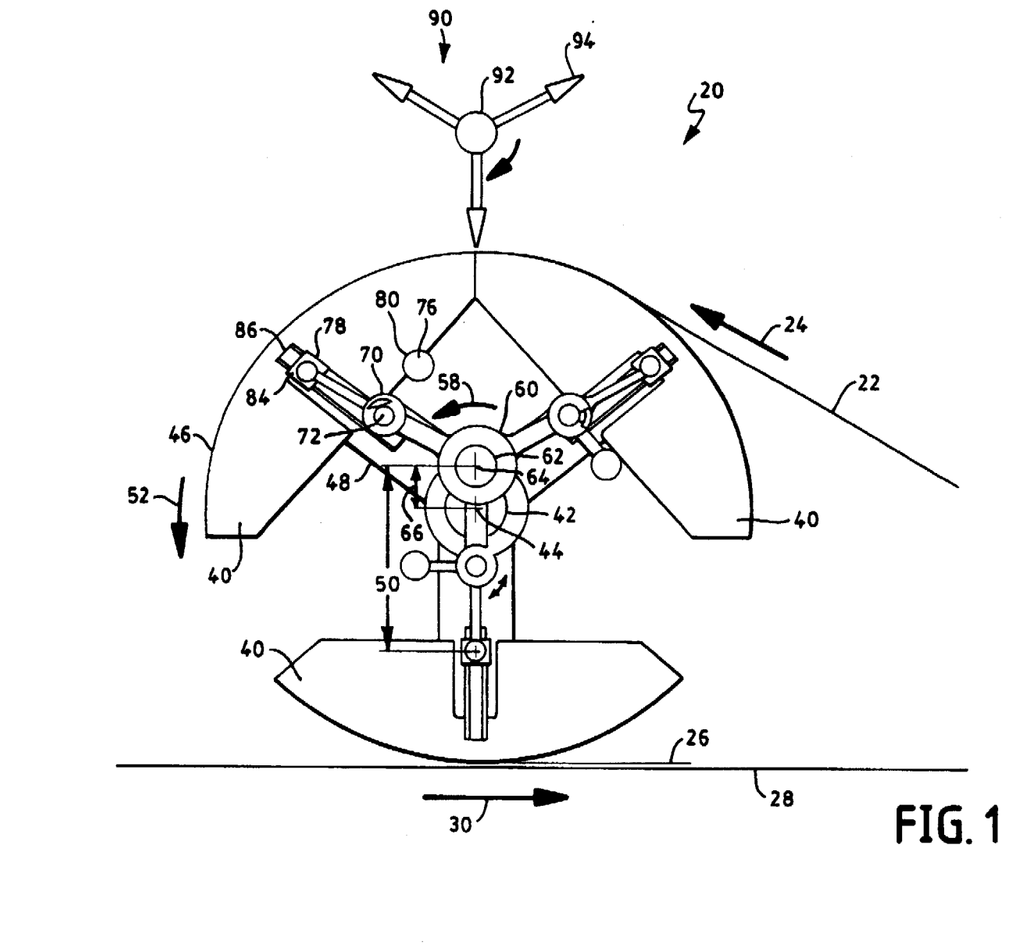
FIG. 1 representatively shows a front elevational view of one example of an apparatus of the present invention.
Figure 2:
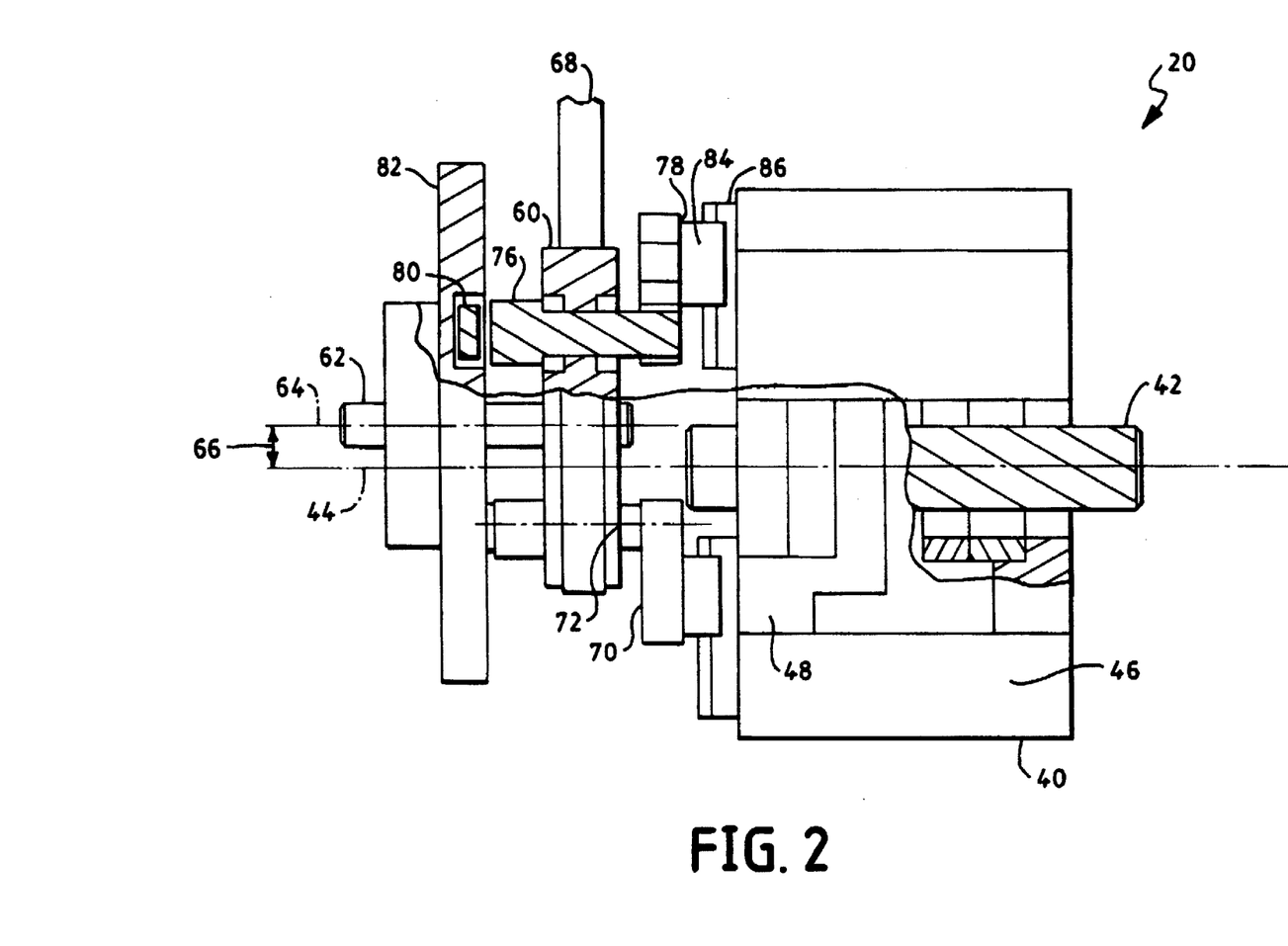
FIG. 2 representatively shows a partially cut away side elevational view of the apparatus of FIG. 1.

Referring now to FIGS. 1 and 2, there is representatively shown an aspect of the invention wherein an apparatus generally indicated at 20 receives a first substrate web 22 traveling at a first speed in the direction indicated by the arrow 24 associated therewith, severs the first substrate web 22 into discrete parts 26 and applies the discrete parts 26 to a second substrate web 28 traveling at a second speed in the direction indicated by the arrow 30 associated therewith. The illustrated example of the apparatus 20 comprises three transfer segments 40 which are configured to receive and apply the discrete parts 26. It should be readily understood that the apparatus 20 may include any number of transfer segments depending upon the different web speeds and desired placement and size of the discrete parts 26. Each transfer segment 40 is configured to be rotated by a drive ring 60 such that the surface speed of each transfer segment 40 is substantially equal to the speed of the first substrate web 22 as the discrete parts 26 are received and substantially equal to the speed of the second substrate web 28 as the discrete parts 26 are applied.

As representatively illustrated in FIGS. 1 and 2, each transfer segment 40 is coaxially supported and rotatably connected to a common idler shaft 42 on a first axis 44. The transfer segments 40 are configured to rotate about the first axis 44 in the direction indicated by the arrow 52 associated therewith. Each transfer segment 40 includes an outer surface 46 and a support member 48 which is rotatably connected to the idler shaft 42 such that each transfer segment 40 can be rotated independently. The radial inner end of the support member 48 of each transfer segment 40 may be rotatably connected to the idler shaft 42 by any technique known to those skilled in the art such as, for example, using conventional bearings. Similarly, the other components of the apparatus 20 of the present invention can be rotatably connected together employing such conventional techniques.

The outer surface 46 of each transfer segment 40 travels along and defines a common circumferential path that allows the discrete parts 26 to be received and applied to the second substrate web 28. The outer surface 46 is configured to receive at least one discrete part 26 and apply the discrete part 26 to the second substrate web 28 each revolution. For example, if the apparatus 20 of the present invention is being used to apply leg elastics to a continuously moving product web of interconnected disposable diapers, the outer surface 46 of each transfer segment 40 may be configured to receive two elongated elastic segments and apply the elongated segments along the leg opening regions on each diaper. In a particular aspect, the outer surface 46 of each transfer segment 40 may also be configured to rotate the discrete parts 26 before the discrete parts 26 are applied to the second substrate web 28. For example, as reepresentatively illustrated in FIG. 4, the outer surface 46 of each transfer segment 46 may be connected to a turning mechanism 110 which is configured to rotate the discrete parts before being applied. Such a configuration is particularly desirable for applying waist elastics to a continuously moving web of interconnected disposable diapers.

In a particular aspect, the outer surface 46 of each transfer segment 40 may be textured to define a surface roughness which assists in gripping and maintaining the discrete parts 26 on the outer surface 46. Such a configuration is particularly desirable when the discrete parts 26 are elongated elastic segments. As used herein, the term "surface roughness" is the surface roughness of a material as determined by conventional methods known to those skilled in the art. One such method utilizes a profilometer to detect the surface roughness. The stylus of the profilometer is drawn across the textured surface a distance of 1.27 centimeters. The profilometer measures the number of peaks and valleys on the surface as well as the magnitude of each. The profilometer automatically calculates the surface roughness as a Roughness Average ($R_a$) which is the arithmetic average of the measured profile height deviations taken within the sampling length and measured from the graphical centerline. The outer surface 46 of each transfer segment 40 may define a surface roughness of at least about 3 micrometers, desirably at least about 10 micrometers and more desirably at least about 15 micrometers. For example, the outer surface 46 may have a surface roughness of from about 5 to about 50 micrometers and desirably from about 10 to about 20 micrometers. To achieve the surface roughness, the outer surface 46 of each transfer segment may also include a coating such as a plasma coating as are known to those skilled in the art. In a particular aspect wherein the discrete parts 46 being received and applied by the transfer segment 40 are elongated elastic parts, it is desirable that the outer surface 46 have a plasma coating which defines a surface roughness of at least about 5 micrometers.

To assist in maintaining the discrete parts 26 on the outer surface 46 of each transfer segment 40, the outer surface 46 may also include a plurality of holes therein through which a relatively low pressure or vacuum can be drawn. The use of such vacuum is particularly desirable when the apparatus 20 of the present invention is used to receive and apply discrete parts 26 which are elongated elastic parts such as leg elastics for application on disposable diapers. The number and pattern of the holes through which the vacuum may be drawn may vary depending upon the size of the transfer segment 40, the shape and size of the discrete parts 26 and the desired location of the discrete parts 26 on the transfer segment 40. If vacuum is desired, typically only a relatively small amount of vacuum is needed to assist the rough outer surface 46 of the transfer segments 40 to maintain the discrete parts 26 on the outer surface 46. For example, typically no more than about 20 inches of water and desirably only from about 0 to about 10 inches of water are required to assist the rough outer surface 46. Applicants have discovered that, when compared to conventional methods which use relatively high levels of vacuum to grip the parts, the combination of the rough outer surface 46 and the relatively low level of vacuum of the apparatus of the present invention provide improved control and placement of the discrete parts 26 on the substrate web 28 at a relatively lower cost.

If vacuum is desired, the vacuum may be drawn through the holes in the outer surface 46 by one or more sources of vacuum using conventional techniques for drawing a vacuum as are known to those skilled in the art. The vacuum to each transfer segment 40 may also be controlled such that a vacuum is only being drawn from the outer surface 46 of each transfer segment for the period of it's rotation when the discrete parts 26 are located on the outer surface 46. For example, the vacuum may be activated just prior to the discrete parts 26 being received and inactivated immediately after the discrete parts 26 are applied to the substrate web 28.

The dimensions of the transfer segments 40 will vary depending upon the desired number of transfer segments 40 and the size and shape of the discrete parts 26 being transferred. For example, when the apparatus 20 includes three transfer segments 40 as representatively illustrated in FIGS. 1 and 2, each transfer segment 40 may have an outer, peripheral arc length spanning of from about 20 degrees to about 120 degrees, an outer radius of from about 5 centimeters to about 50 centimeters, and a width of from about 5 centimeters to about 40 centimeters.

The apparatus 20, as representatively shown in FIGS. 1 and 2, further comprises a drive ring 60 which is configured to rotate each transfer segment 40 at a variable speed. The inner radial end of the drive ring 60 is rotatably connected to a fixed shaft 62 on a second axis 64. The drive ring 60 is configured to be rotated at a constant speed about the second axis 64 by a driving means 68 in the direction indicated by the arrow 58 associated therewith. The driving means 68 may include a motor operatively connected through suitable gearing and drive belts to the drive ring 60. Thus, in use, the motor rotates the drive ring, which, in turn, rotates the transfer segments 40 at the desired variable speed.

To provide the desired variable speed of each transfer segment 40, the second axis 64 of the drive ring 60 is offset from the first axis 44 of the transfer segments 40 by an offset distance 66. The offset distance 66 between the first axis 44 and the second axis 64 may be any distance which provides the desired variations in the speed of the outer surface 46 of each transfer segment 40. For example, the offset distance 66 may be at least about 0.1 centimeters, desirably from about 0.1 to about 7.5 centimeters and more desirably from about 2.5 to about 5.0 centimeters.

The apparatus 20 further comprises at least one coupler arm 70 which is pivotally connected to the drive ring 60 about a pivot point 72. The apparatus 20 typically includes one coupler arm 70 for each transfer segment 40. Accordingly, in the apparatus 20 representatively illustrated in FIGS. 1 and 2 which includes three transfer segments 40, three coupler arms 70 independently connect the drive ring 60 to each respective transfer segment 40. The coupler arms 70 are pivotally connected to the drive ring 60 about pivot points 72 which are selectively located to provide the desired speeds for the transfer segments 40. In a particular aspect, the pivot points 72 for the coupler arms 70 are located the same distance radially outward from the axis 64 of the drive ring 60. In such a configuration, the pivot points 72 rotate at a constant speed along a common circumferential path as the drive ring 60 is rotated at a constant speed. The coupler arms 70 may be pivotally connected to the drive ring 60 by conventional means known to those skilled in the art. For example, a bearing which is commercially available from SKF Industries, Inc., a business having offices located in King of Prussia, Pa., may be used to pivotally connect the coupler arms 70 to the drive ring 60 at the pivot points 72.

Each coupler arm 70, as representatively illustrated in FIGS. 1 and 2, includes a cam end 76 and a crank end 78 which extend radially outward from the pivot point 72. The cam end 76 and crank end 78 are designed to remain at a fixed angle relative to each other. For example, a first line extending through the pivot point 72 and the cam end 76 and a second line extending through the pivot point 72 and the crank end 78 may define an angle of from about 30 to about 180 degrees and desirably from about 60 to about 120 degrees to provide the desired variable speed. The cam end 76 of each coupler arm 70 is configured to follow a predetermined curvilinear path and the crank end 78 of each coupler arm 70 is slidably connected to a respective transfer segment 40. As the drive ring 60 is rotated, the cam end 76 of each coupler arm 70 is guided along the curvilinear path and the crank end 78 of each coupler arm slidably engages the respective transfer segment 40 thereby pivoting the coupler arm 70 about the pivot point 72. The pivoting of the coupler arm 70 and the offset crank motion of the drive ring 60 vary the effective drive radius 50 of each transfer segment 40 and rotate each transfer segment 40 at a variable speed. In a particular aspect, each coupler arm 70 is configured to pivot at least about 5 degrees and desirably from about 20 to about 60 degrees as the drive ring 60 is rotated to provide the desired changes in the effective drive radius 50 and rotation of each transfer segment 40.

The cam end 76 of each coupler arm 70 may be guided along the curvilinear path by any means known to those skilled in the art. In a particular aspect, as illustrated in FIGS. 1 and 2, the cam end 76 may include a cam follower 80 which is connected to the radially outward end of the cam end 76 and configured to follow the profile of a cam mechanism 82. In such a configuration, the profile of the cam mechanism 82 can be readily changed to change the desired speed output. Suitable cam followers and cam mechanisms are known to those skilled in the art. For example, the cam follower 80 may be one commercially available from INA, a business having offices located in Fort Mills, N.C., under the trade designation NUKR 35. A suitable cam mechanism 82 may be manufactured with any desired profile by methods known to those skilled in the art.

The crank end 78 of each coupler arm 70 may be slidably connected to the respective transfer segment 40 by any means known to those skilled in the art. In a particular aspect as representatively illustrated in FIGS. 1 and 2, an inwardly grooved slide member 84 may be pivotally connected to the radially outward end of the crank end 78 of each coupler arm 70. Each slide member 84 is configured to slide along a rail member 86 which is connected to the support member 48 of the respective transfer segment 40. Each rail member 86 projects outwardly from the transfer segment 40 and may be positioned on the transfer segment 40 in any alignment which provides the desired speeds of the transfer segment 40. Suitable complementary slides and rails are known to those skilled in the art. For example, the slide member 84 and rail member 86 combination may be one commercially available from Star Linear Systems, Inc., a business having offices located in Charlotte, N.C., under the trade designation Ball Rail System-1651-15. Alternatively, the crank end 78 of each coupler arm 70 may include a groove therein which is configured to slidably engage a cam follower located on the respective transfer segments 40.

The apparatus 20, as representatively illustrated in FIGS. 1 and 2, may further include a knife roll 90 to sever the continuously moving first substrate web 22 into the discrete parts 26 that are fed onto each transfer segment 40. The knife roll 90 may be any mechanism known to those skilled in the art that can sever a web of material into discrete segments such as, for example, a rotary cutter. As representatively illustrated in FIG. 1, the knife roll 90 may be connected to and configured to rotate about a shaft 92. The knife roll 90 may further include a plurality of cutting edges 94 which are configured to sever the first substrate web 22 into the discrete parts 26.

Figure 4:
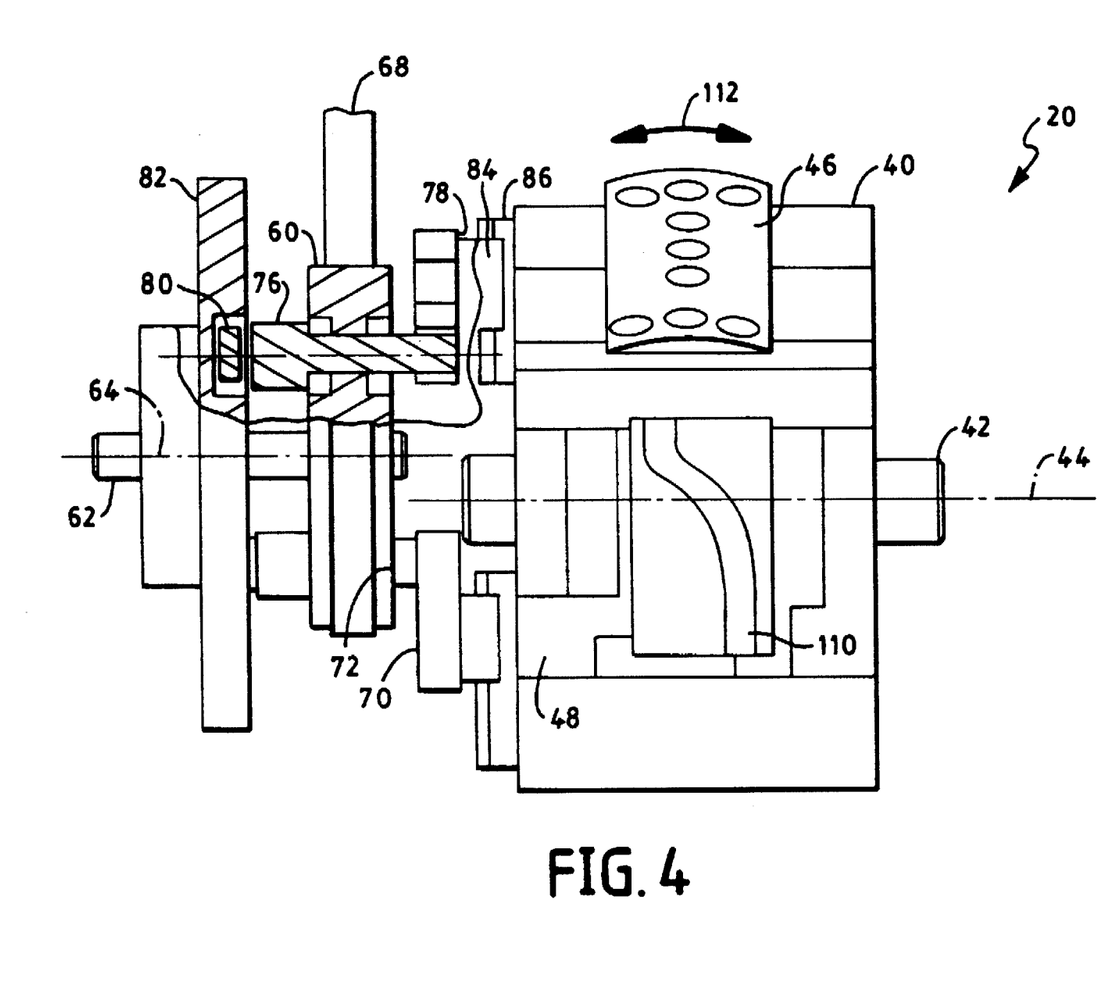
FIG. 4 representatively shows a partially cut away side elevational view of another example of an apparatus of the present invention.

As representatively illustrated in FIG. 4, the apparatus 20 may further include a turning mechanism 110 for rotating the discrete parts 26 before they are applied to the second substrate web 28. Any mechanism which provides the desired rotation of the parts 26 can be used. For example, one suitable mechanism is a barrel cam as are well known to those skilled in the art. Thus, in use, the discrete parts 26 may be received by the transfer segment 40 while oriented in one direction and, subsequently, be rotated by the turning mechanism 110 in the direction indicated by the arrow 112 associated therewith before being applied to the second substrate web 28. The turning mechanism 110 can be configured to rotate the discrete parts 26 any amount before they are applied. For example, the turning mechanism 110 may be configured to rotate the parts 26 from about 1 to about 180 degrees and desirably from about 1 to about 90 degrees before they are applied depending upon the desired orientation of the parts 26 on the second substrate web 28. Such a turning mechanism 110 is particularly useful when applying waist elastics to a product web of interconnected disposable absorbent articles.

It will be apparent that the continuously moving substrate web 22, in certain aspects of the invention, may be omitted and the discrete parts 26 may be placed directly upon each transfer segment 40. In addition, it will be apparent that the discrete parts 26 may be adhered to the second substrate web 28 by means of an adhesive applied in a selected pattern to the surface of the discrete parts 26, or by any other suitable means for adhering the discrete parts 26 to the substrate web 28.

Figure 3:
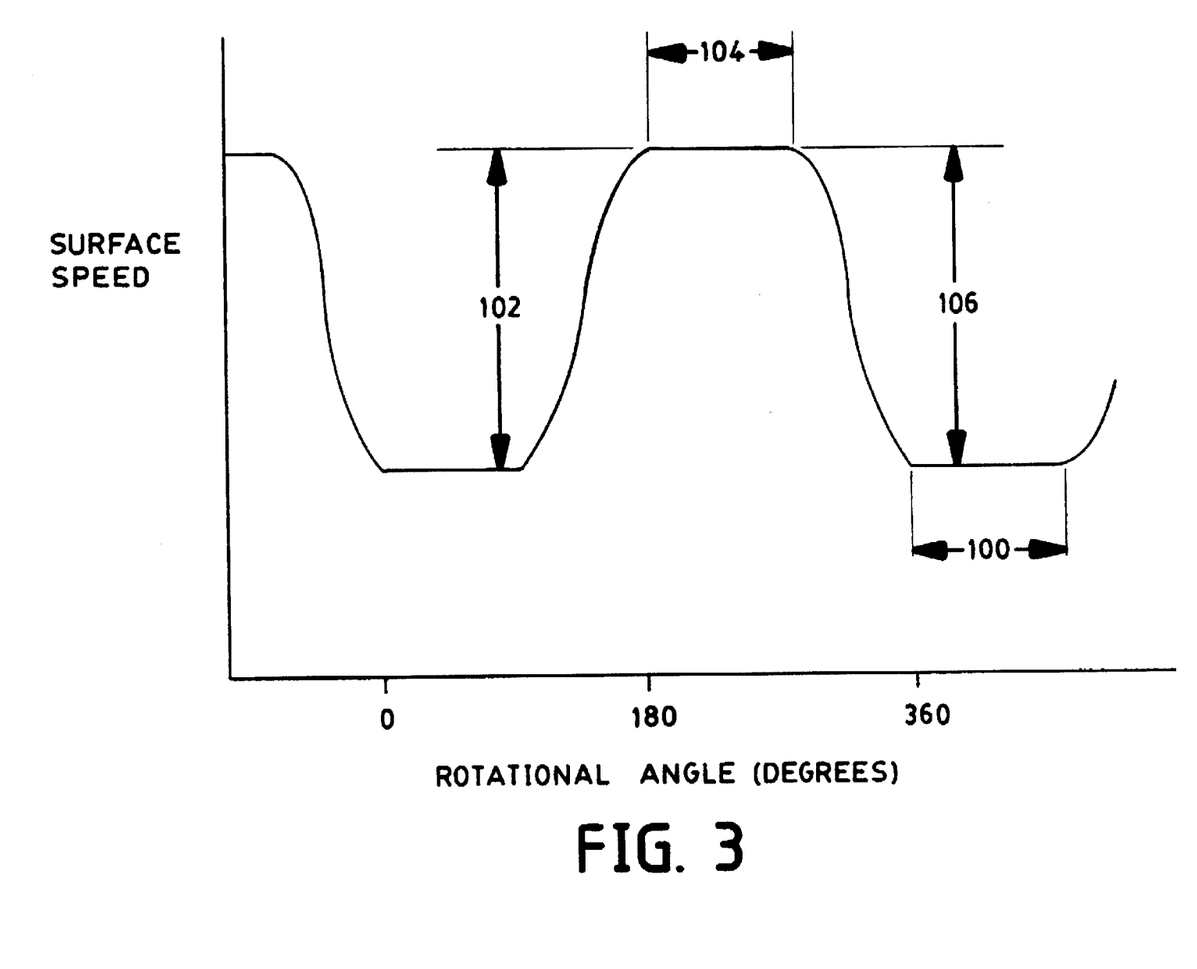
FIG. 3 representatively shows a typical speed profile for the apparatus of FIG. 1.

The use of the combination of the offset drive ring 60 and pivoting coupler arm 70 to drive the transfer segments 40 in the apparatus 20, as representatively illustrated in the various aspects of the invention described above, provides an inexpensive and adaptable method for severing a first substrate web 22 traveling at a speed into discrete parts 26 and applying the discrete parts 26 to a substrate web 28 traveling at a different speed. The design of the drive ring 60 and coupler arm 70 can be analytically determined to obtain the desired output function which can include variable angular velocities with fixed speed dwells. For example, the speed profile of an example of an apparatus 20 according to the different aspects of the present invention is representatively illustrated in FIG. 3. As illustrated, the transfer segments 40 of the apparatus 20 of the present invention can be configured to rotate through a period of low speed dwell 100, acceleration 102, high speed dwell 104 and deceleration 106 in each revolution.

As the offset drive ring 60 rotates at a constant speed, each coupler arm 70 pivots about the pivot points 72 as the cam end 76 of the coupler arm 70 is guided along the profile of the cam 82 and the crank end of the coupler arm 70 slidably engages the respective transfer segment 40. As a result, the effective drive radius 50 for each transfer segment 40 is varied thereby varying the surface speed of each transfer segment 40 independently. The periods of acceleration 102 and deceleration 106 of each transfer segment 40 are provided by the offset crank motion which results from the axis 64 of the drive ring 60 being offset from the axis 44 of the transfer segments 40. Whereas, the periods of low speed dwell 100 and high speed dwell 104 are provided by the pivoting action of each coupler arm 70 about the pivot points 72 as the drive ring 60 is rotated. As such, the combination of the offset drive ring 60 and the pivoting coupler arm 70 of the apparatus 20 of the present invention can provide both the desired changes in speed and the desired periods of constant speed to effectively receive and apply the discrete parts 26 onto the substrate web 28 in the desired spaced apart locations.

As compared to conventional methods, such as the slip gap method described above, for changing the speed of a discrete part such that it can be applied to a continuously moving web, the use of the combination of the offset drive ring 60 and the pivoting coupler arm 70 of the present invention provides the ability to obtain greater changes in speed and to maintain constant speeds for a fixed duration. The fixed speed dwell achieved by using the apparatus of the present invention can be accurately and inexpensively designed to precisely control the length and placement of the discrete parts 26 on the substrate web 28. For example, in the various aspects of the invention, the drive ring 60 and coupler arm 70 are analytically designed such that each transfer segment 40 receives the discrete parts 26 while maintaining a constant surface speed substantially equal to the speed of the first substrate web 22 and applies the discrete parts 26 to the second substrate web 28 while maintaining a constant surface speed which is substantially equal to the speed of the second substrate web 28.

In a particular aspect, the surface speed of each transfer segment 40 is maintained substantially constant as the discrete parts 26 are received or applied for at least about 10 degrees of rotation and desirably at least about 20 degrees of rotation of the transfer segment. For example, the surface speed of each transfer segment may be maintained substantially constant as the parts are received or applied for from about 5 to about 120 degrees of rotation, desirably from about 15 to about 90 degrees of rotation, and more desirably from about 45 to about 60 degrees of rotation of the respective transfer segment 40. In addition, the surface speed increase or decrease of the transfer segment 40 as it moves from receiving the discrete parts 26 to applying the discrete parts 26 and back again defines a speed ratio of from about 0.1:1 to about 0.99:1, desirably from about 0.38:1 to about 0.75:1, and more desirably from about 0.4:1 to about 0.6:1. The term "speed ratio", as used herein, defines the ratio of the surface speed of the transfer segment 40 at the low speed dwell 100 to the surface speed of the transfer segment 40 at the high speed dwell 104 as representatively illustrated in FIG. 3.

The apparatus and method of the present invention may be used in the manufacture of articles such as diapers, training pants, and adult incontinence products, among other uses. In particular, the apparatus and method may be used to apply discrete parts or components, such as, for example, waist elastic, leg elastic, tapes, snaps, and hook and loop materials to the diaper or incontinence product. Articles such as diapers and incontinence products are described, for example, in U.S. Pat. Nos. 4,704,116 issued Nov. 3, 1987, to Enloe; 4,798,603 issued Jan. 17, 1989, to Meyer et al.; 4,710,187 issued Dec. 1, 1987, to Boland et al.; 4,770,656 issued Sep. 13, 1988, to Proxmire et al.; and 4,762,521 issued Aug. 9, 1988 to Roessler et al.; the disclosures of which are incorporated by reference.

In a particular aspect, the apparatus 20 of the present invention may be used to apply elongated elastic parts to the leg opening regions on a product web of interconnected disposable diapers. For example, a continuously moving web of elongated elastic material 22 may be fed into the knife roll 90. The web of elastic material may be elongated at least about 150 percent and desirably from about 150 to about 400 percent before being severed. The knife roll 90 severs the web of elongated elastic material 22 into discrete elongated elastic parts 26 that are fed onto each transfer segment 40. The elongated elastic parts 26 are held onto the outer surface 46 of each transfer segment 40 as it rotates in the elongated state by the surface roughness of the outer surface 46. In a particular aspect, the elongated elastic parts 26 are maintained at an elongation of at least about 125 percent, desirably at least about 150 percent, and more desirably from about 150 to about 400 percent until they are applied to the product web. In addition, a relatively low level of vacuum may also be drawn through holes in the outer surface 46 to assist the surface roughness in maintaining the elongated elastic parts 26 in the elongated state.

The combination of the offset drive ring 60 and the pivoting coupler arm 70 are rotated by the drive means 68 which, in turn, rotates each transfer segment 40 at the desired variable speed with fixed speed dwells. As each transfer segment 40 is rotated, the outer surface 46 of each transfer segment 40 maintains a substantially constant speed as the discrete elongated elastic parts 26 are received and applied. In particular, each transfer segment 40 receives the elongated elastic parts 26 while maintaining a constant surface speed substantially equal to the speed of the web of elongated elastic material 22. The surface speed of each transfer segment 40 then changes to a second constant surface speed such that the speed of the discrete elongated elastic parts 26 being transferred is substantially equal to the speed of the continuously moving product web of interconnected diapers as the elongated elastic parts 22 are applied to the leg opening regions on each diaper. The surface speed of each transfer segment 40 is then changed back to substantially equal the speed of the web of elongated elastic material 22 before the next discrete elongated elastic part 26 is received.

The discrete elongated elastic parts 22 being applied to the web of interconnected diapers 28 may be made of any suitable material having elastic or stretchable properties. Examples of such materials include films or layers of natural rubber, synthetic rubber, or thermoplastic elastomeric polymers, and can be panels, or single, or multiple threads or filaments or ribbons thereof. These materials may also be heat-shrinkable or heat-elasticizable. Furthermore, these stretchable materials may be formed with gatherable layers, such as spunbonded polymer materials, as a stretch-bonded laminate. For example, a suitable stretch-bonded laminate comprise two gatherable layers of 0.4 ounce per square yard of spunbond polypropylene having therebetween a layer of meltblown elastic material such as a Kraton elastic in either layer form or separate threads of material having a basis weight of about 0.5 ounce per square yard. The layer of the elastomeric is stretched, the two layers of polypropylene then joined to the elastomeric layer, and upon relaxing the layers, the polypropylene layers gather. The materials may be breathable or nonbreathable.

Although the above representative example concerns the application of leg elastic to a diaper, it should be readily apparent to those of ordinary skill in the art that the present invention may be utilized in any circumstance requiring speed variations and constant speed dwells when transferring parts onto a moving web.

While the invention has been described in detail with respect to specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

What is claimed is:

1. A method for severing an elongated elastic web traveling at a first speed into discrete elongated elastic parts and applying said elongated elastic parts in a spaced apart relationship onto a product web of interconnected disposable absorbent articles traveling at a second speed, said method comprising the steps of:

a) supplying said elongated elastic web at said first speed and said product web at said second speed;

b) severing said elongated elastic web into said discrete elongated elastic parts;

c) rotating a plurality of transfer segments about a common first axis at a variable speed wherein said step of rotating includes the steps of:

i) providing a drive ring which is rotatable about a second axis which is offset from said first axis;

ii) providing a plurality of coupler arms each of which is pivotally connected to said drive ring about a respective pivot point which is located radially outward from said second axis wherein each of said coupler arms includes a cam end which is configured to follow a predetermined curvilinear path and a crank end which is slidably connected to a respective one of said transfer segments; and iii) rotating said drive ring about said second axis thereby guiding said cam end along said curvilinear path and slidably engaging said crank end with said respective transfer segment to pivot each of said coupler arms about said respective pivot points to independently vary an effective drive radius of each of said transfer segments and rotate said transfer segments at said variable speed;

d) transferring each of said discrete elongated elastic parts onto an outer surface of said respective transfer segment while said respective transfer segment is rotating at a first surface speed which is substantially equal to said first speed of said elongated elastic web; and e) applying each of said elongated elastic parts onto said product web while said respective transfer segment is rotating at a second surface speed which is substantially equal to said second speed of said product web.

2. The method of claim 1 wherein said pivoting of said coupler arms maintains said first surface speed of said transfer segments substantially constant as said elongated elastic parts are received and maintains said second surface speed of said transfer segments substantially constant as said elongated elastic parts are applied to said product web.

3. The method of claim 2 wherein said first surface speed and said second surface speed are maintained substantially constant for at least 10 degrees of rotation of said respective transfer segment.

4. The method of claim 1 wherein said first surface speed and said second surface speed define a speed ratio of from 0.38:1 to 0.75:1.

5. The method of claim 1 wherein said second axis of said drive ring is offset from said first axis of said transfer segments by a distance of at least 0.1 centimeters.

6. The method of claim 1 and further comprising the step of elongating said elastic web at least 150 percent.

7. The method of claim 1 further including the step of maintaining said discrete elongated elastic parts at an elongation of at least 125 percent until said elongated elastic parts are applied to said product web.

8. The method of claim 7 wherein said step of maintaining said discrete elongated elastic parts at said elongation further includes the step of selecting said outer surface of said transfer segments to define a surface roughness of at least 3 micrometers.

9. The method of claim 8 wherein said step of maintaining said discrete elongated elastic parts at said elongation further includes the step of drawing a vacuum through a plurality of openings defined in said outer surface of each of said transfer segments.

10. The method of claim 1 and further comprising rotating said outer surface of said transfer segment with respect to a direction of rotation of said transfer segment to rotate said discrete elongated elastic parts before said parts are applied to said product web.

11. The method of claim 10 wherein said discrete elongated elastic parts are rotated from 1 to 90 degrees before being applied to said product web.

12. A method for severing a first substrate web traveling at a first speed into discrete parts and applying said discrete parts onto a second substrate web traveling at a second speed, said method comprising the steps of:
 a) supplying said first substrate web at said first speed and said second substrate web at said second speed;
 b) severing said first substrate web into said discrete parts;
 c) rotating at least one transfer segment about a first axis at a variable speed wherein said step of rotating includes the steps of:
  i) providing a drive ring which is rotatable about a second axis which is offset from said first axis;
  ii) providing a coupler arm which is pivotally connected to said drive ring about a pivot point located radially outward from said second axis wherein said coupler arm includes a cam end which is configured to follow a predetermined curvilinear path and a crank end which is slidably connected to said transfer segment; and
  iii) rotating said drive ring about said second axis thereby guiding said cam end along said curvilinear path and slidably engaging said crank end with said transfer segment to pivot said coupler arm about said pivot point to selectively vary an effective drive radius of said transfer segment and rotate said transfer segment at said variable speed;
 d) transferring said discrete parts onto an outer surface of said transfer segment while said transfer segment is rotating at a first surface speed; and
 e) applying said discrete parts onto said second substrate web while said transfer segment is rotating at a second surface speed.

13. The method of claim 12 wherein said first surface speed of said transfer segments is substantially equal to said first speed of said first substrate web and said second surface speed of said transfer segments is substantially equal to said second speed of said second substrate web.

14. The method of claim 12 wherein said pivoting of said coupler arm maintains said first surface speed of said transfer segment substantially constant as said discrete parts are received and maintains said second surface speed of said transfer segment substantially constant as said discrete parts are applied to said second substrate web.

15. The method of claim 14 wherein said first surface speed and said second surface speed are maintained substantially constant for at least 10 degrees of rotation of said transfer segment.

16. The method of claim 12 wherein said first surface speed of said transfer segment is less than said second speed of said transfer segment such that said discrete parts are applied to said second substrate web in a spaced apart relationship.

17. The method of claim 16 wherein said first surface speed and said second surface speed define a speed ratio of from 0.1:1 to 0.99:1.

18. The method of claim 12 wherein said second axis of said drive ring is offset from said first axis of said transfer segment by a distance of at least 0.1 centimeters.

19. The method of claim 12 wherein said crank end of said coupler arm includes a groove therein which slidably engages a cam follower located on said transfer segment as said drive ring is rotated.

20. The method of claim 12 wherein said crank end of said coupler arm includes a slide member which pivots about said crank end and slidably engages a rail member located on said transfer segment as said drive ring is rotated.

21. The method of claim 12 wherein said step of rotating said drive ring pivots said coupler arm about said pivot point at least 5 degrees.

22. The method of claim 12 and further comprising rotating said outer surface of said transfer segment with respect to a direction of rotation of said transfer segment to rotate said discrete parts before said parts are applied to said second substrate web.

23. The method of claim 22 wherein said discrete parts are rotated from 1 to 90 degrees before being applied to said second substrate web.

* * * * *